(12) United States Patent
Barry

(10) Patent No.: US 11,305,025 B1
(45) Date of Patent: Apr. 19, 2022

(54) DISINFECTANT APPARATUS

(71) Applicant: Robert Barry, Franklin, MA (US)

(72) Inventor: Robert Barry, Franklin, MA (US)

( * ) Notice: Subject to any disclaimer, the term of this patent is extended or adjusted under 35 U.S.C. 154(b) by 38 days.

(21) Appl. No.: 16/900,134

(22) Filed: Jun. 12, 2020

Related U.S. Application Data

(60) Provisional application No. 63/016,428, filed on Apr. 28, 2020.

(51) Int. Cl.
*A61L 2/10* (2006.01)
*A61L 2/00* (2006.01)
*A61L 2/24* (2006.01)

(52) U.S. Cl.
CPC ............... *A61L 2/0047* (2013.01); *A61L 2/24* (2013.01); *A61L 2202/11* (2013.01); *A61L 2202/14* (2013.01)

(58) Field of Classification Search
CPC . A61L 2/10; A61L 2/0047; A61L 2/24; A61L 2202/11; A61L 2202/14
See application file for complete search history.

(56) References Cited

U.S. PATENT DOCUMENTS

| 6,730,265 | B2 | 5/2004 | Horton, III |
|---|---|---|---|
| 8,318,090 | B2 * | 11/2012 | Gordon ................ A61N 5/0613 422/1 |
| 8,662,705 | B2 * | 3/2014 | Roberts .................... A61L 2/10 362/249.02 |
| 10,010,634 | B2 | 7/2018 | Bonutti et al. |
| 10,549,000 | B2 | 2/2020 | Kellen et al. |
| 10,639,387 | B2 * | 5/2020 | Bonutti .................... A61L 2/10 |
| 10,814,025 | B2 * | 10/2020 | Bonutti .................... A61L 2/025 |
| 10,849,996 | B2 * | 12/2020 | Shur .................... H04N 7/183 |
| 10,940,220 | B2 * | 3/2021 | Crosby ................ A61L 2/0047 |
| 10,967,081 | B2 * | 4/2021 | Cole .................... A61L 2/0047 |
| 10,994,040 | B2 * | 5/2021 | Kennedy .................... A61L 2/10 |
| 11,033,643 | B2 * | 6/2021 | Starkweather ............ A61L 2/24 |
| 11,135,324 | B2 * | 10/2021 | Rosen .................... A61L 2/0052 |
| 2010/0266446 | A1 * | 10/2010 | Constantacos ........ A61L 2/0047 422/107 |
| 2016/0303265 | A1 | 10/2016 | Coles |
| 2017/0296686 | A1 * | 10/2017 | Cole .......................... A61L 2/10 |
| 2018/0214588 | A1 * | 8/2018 | Casares .................. A61L 2/202 |
| 2018/0373157 | A1 * | 12/2018 | Kimsey-Lin .............. A61L 2/10 |
| 2019/0117802 | A1 * | 4/2019 | Hishinuma ............ A47K 10/48 |
| 2019/0154439 | A1 | 5/2019 | Binder |
| 2020/0261608 | A1 * | 8/2020 | Crosby .................... A61L 2/10 |

(Continued)

FOREIGN PATENT DOCUMENTS

WO   2012084319   6/2012

*Primary Examiner* — Wyatt A Stoffa
(74) *Attorney, Agent, or Firm* — Salter & Michaelson

(57) ABSTRACT

A disinfectant device includes a housing, a UV source disposed within the housing, a reflector for directing rays from the UV source downward through a bottom of the housing, a motion detector, a frequency detector, and an indicator light, said UV source specific to a non-visible light spectrum in a range of 200 nm to 222 nm. The bottom can be an open bottom or may include a glass covering. A timer can be included to display a duration for the UV source to be turned on. The device can include a protective curtain about a perimeter of the bottom of the housing. The reflector can be ellipsoidal in shape to direct the rays from the UV source downward through the bottom of the housing.

7 Claims, 7 Drawing Sheets

(56) References Cited

U.S. PATENT DOCUMENTS

| | | | |
|---|---|---|---|
| 2021/0046198 A1* | 2/2021 | Winslow | A61L 2/26 |
| 2021/0063891 A1* | 3/2021 | Kimsey-Lin | A61L 2/24 |
| 2021/0145994 A1* | 5/2021 | Dombrowsky | H05B 45/22 |
| 2021/0196845 A1* | 7/2021 | Crosby | A61L 2/0047 |
| 2021/0252305 A1* | 8/2021 | Randers-Pehrson | A61B 18/18 |
| 2021/0299290 A1* | 9/2021 | Maxik | A61L 2/26 |
| 2021/0299300 A1* | 9/2021 | Mullen | A61L 2/0052 |
| 2021/0316022 A1* | 10/2021 | Ciesiun | A61L 2/10 |
| 2021/0316025 A1* | 10/2021 | Cole | A61L 2/26 |

\* cited by examiner

DISINFECTANT APPARATUS

RELATED CASES

Priority for this application is hereby claimed under 35 U.S.C. § 119(e) to commonly owned and U.S. Provisional Patent Application No. 63/016,428 which was filed on Apr. 28, 2020 and which is incorporated by reference herein in its entirety.

FIELD OF THE INVENTION

The present invention relates in general to a disinfectant device or apparatus and pertains more particularly to such a device or apparatus that is focused on the use of far UVC (Ultraviolet-C) rays.

BACKGROUND OF THE INVENTION

Many viruses spread from person to person mainly through fine liquid droplets, or aerosols, that become airborne when people with flu or another virus cough, sneeze, or talk. Much of this material is attracted to and ends up on our hands.

Accordingly, it is an object of the present invention to provide an improved device that prevents the formation of viruses.

SUMMARY

The apparatus or device of the present invention is designed to be mounted typically in a household bathroom near a vanity or sink. Additionally, the device can be mounted at any convenient location in the house or public dwelling. An individual rubs their hands under the device for 15-20 seconds as if washing your hands, thereby killing many of the bacteria and viruses on the hands. This activity can be done before or after washing of hands or routinely during the day as one enters or leaves their house and as one enters or leaves a public location. The use of the UV lamp or UV LED can, in some cases be used in addition to, or instead of, handwashing. Thus, a user can simply place their hands underneath and disinfect their hands within 20 seconds, without having to wait for water to get warm, without the need for soap, and without the need to try hands after disinfecting. This apparatus and its function can also be used in restaurants, food handling facilities, hospitals, or doctor's offices and other locations where hand sanitization is needed.

In an embodiment, a disinfectant device includes a housing, a UV light source either lamp based or UV light-emitting diode (LED) disposed within the housing, a reflector for directing rays from the UV source downward through a bottom of the housing, a motion detector, a frequency detector, and an indicator light, said UV source is specific to a non-visible light spectrum in a range of 200 nm to 222 nm.

The disinfectant device can have an open bottom. In some embodiments, rather than an open bottom, the device can further include a glass covering on the bottom of the housing, the glass covering disposed between the UV source and hands when placed under the housing. The device can further include a timer on an exterior of the housing to indicate a duration of the UV source being turned on. The indicator light can be on the exterior on a same surface as the timer. The reflector can be ellipsoidal in shape. The housing can be solid without any openings except for the bottom. The housing can have a width of at least 4-inches, a height of at least 4-inches and a length of at least 4-inches. The housing can have a maximum width of 24-inches, a maximum height of 24-inches and a maximum length of 24-inches. The disinfectant device can further include a protective curtain disposed about a perimeter of the bottom of the housing.

A disinfectant device can include a housing that is fully-enclosed and includes a top, a front, a back, a first side, and a second side, that together form the housing, a UV source disposed within the housing such that UV rays are directed downward through a bottom of the housing, a motion detector configured to detect hands under a bottom of the housing and to transmit a signal to turn the UV source on for a predetermined period of time when hands are detected under the bottom of the housing, and an indicator light or a timer to convey the UV source is on for the predetermined period of time.

The disinfectant device can further include a frequency detector configured to detect a frequency of the UV rays. The disinfectant device UV lamp is specific to a non-visible light spectrum in a range on the order of 200 nm to 222 nm. The disinfectant device can include both the indicator light and the timer, wherein the indicator light can be disposed on the front of the housing, wherein the timer can be disposed on the front of the housing, wherein the UV source can be positioned proximate a top of the housing, wherein the frequency detector can be positioned on the back of the housing, and wherein an AC power supply is coupled to the UV source, to the frequency detector, to the indicator light, and to the motion detector. The disinfectant device can further include a glass covering on the bottom of the housing, the glass covering disposed between the UV source and hands when placed under the housing. The timer can be on the front of the housing to indicate a duration of the UV source being turned on, and wherein the indicator light is on the front of the housing. The housing can be solid without any openings except for an open bottom.

A disinfectant device includes a housing that is fully-enclosed and includes a top, a front, a back, a first side, and a second side, that together form the housing, a UV source disposed within the housing such that UV rays are directed downward through a bottom of the housing, said UV source specific to a non-visible light spectrum in a range of 200 nm to 222 nm, a motion detector configured to detect hands under a bottom of the housing and to transmit a signal to turn the UV source on for a predetermined period of time when hands are detected under the bottom of the housing, and an indicator light or a timer to convey the UV source is on for the predetermined period of time. The housing can have a width of at least 4-inches, a height of at least 4-inches and a length of at least 4-inches.

The disinfectant device can have an open bottom or can include a glass covering on the bottom of the housing, with the glass covering disposed between the UV source and hands when placed under the housing. The disinfectant device can further include a protective curtain disposed about a perimeter of the bottom of the housing.

BRIEF DESCRIPTION OF THE DRAWINGS

It should be understood that the drawings are provided for the purpose of illustration only and are not intended to define the limits of the disclosure. The foregoing and other objects and advantages of the embodiments described herein will become apparent with reference to the following detailed description when taken in conjunction with the accompanying drawings in which.

DETAILED DESCRIPTION

In accordance with the present invention as illustrated in FIGS. 1-7, there is provided a disinfectant device comprised of a housing, a UV source (lamp or LED) disposed within the housing, a reflector for directing rays form the UV source downward through a bottom of the housing, a motion detector, a frequency detector and an indicator light. The UV source can emit rays of light in the non-visible light spectrum in a range of 200 nm to 222 nm in wavelength.

It is known that long exposure to conventional germicidal UV light can be a human health hazard and can lead to skin cancer and cataracts. However, in accordance with the present invention it has been surprisingly found that low doses of far ultraviolet C (far-UVC, example 200 nm-222 nm) light is capable of killing many viruses without harming the human tissue. A very low dose of 200 nm to 222 nm light, has a very limited range and cannot penetrate through the outer layer of human skin or the tear layer in the eye. Therefore, it is not a human health hazard but because viruses and bacteria are much smaller than human cells, far-UVC light can reach their DNA and kill them.

In accordance with the present invention there is provided the rubbing of the hands under a continuous very low dose of 200 nm to 222 nm, far-UVC light for approximately 15-20 seconds which would inactivate and end the life of many bacteria and viruses.

Figure 1:
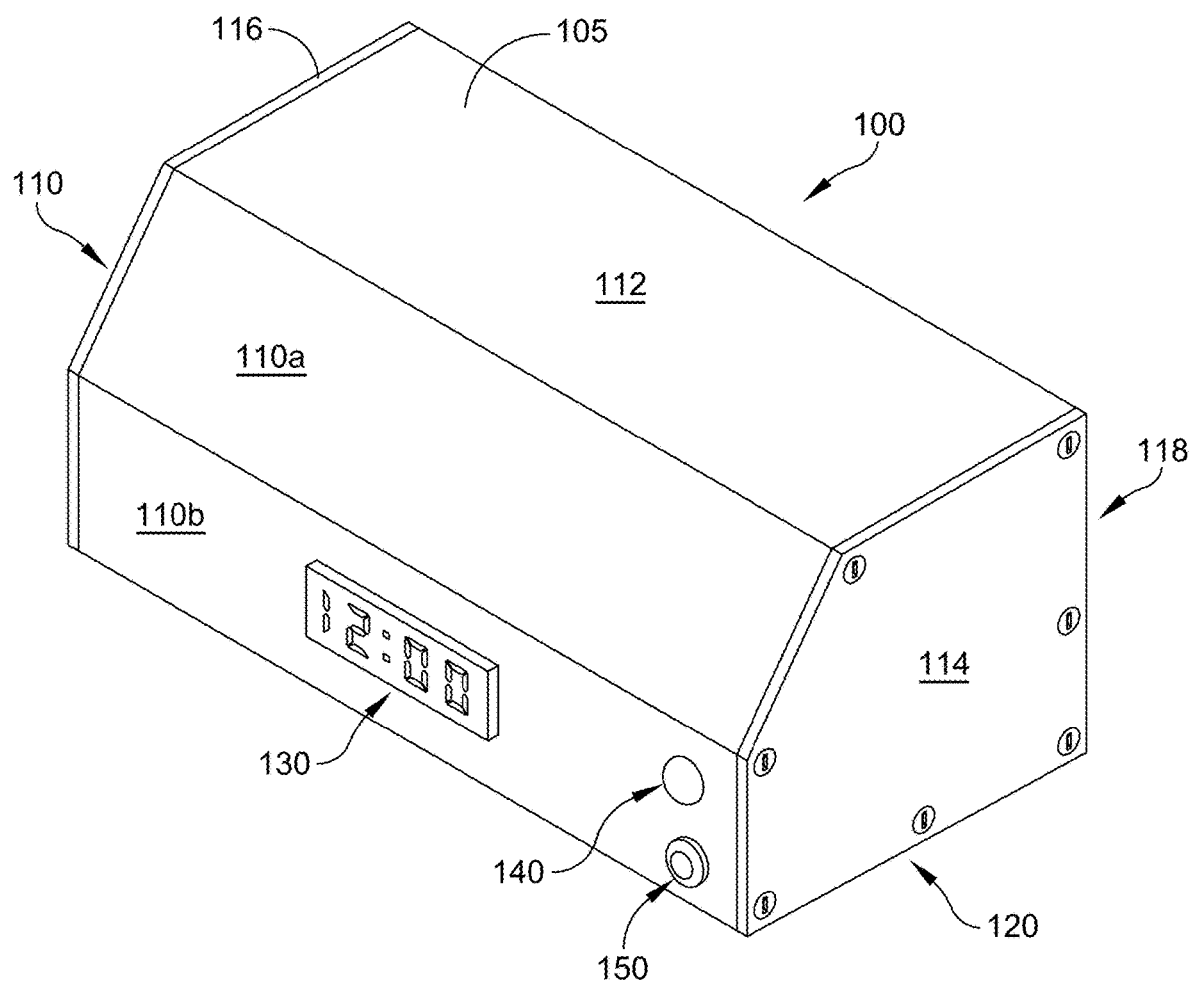
FIG. 1 is a perspective view of a device of apparatus according to the present disclosure.

With reference to the attached drawings, there is provided a device 100 as shown in FIG. 1, showing a perspective view of a device of apparatus according to the present disclosure. The device 100 is comprised of a housing 105 having a front 110, a top 112, a first side 114, a second side 116, a back 118, and a bottom 120. The front 110 can be a flat front or can include two front sections 110a, 110b as shown in FIG. 1. The bottom 120 can be an open bottom or can include a glass covering or other structure, as will be appreciated.

The front section 110b can include a timer 130, an indicator light 140, and a motion detector 150. The timer can indicate a duration of the UV source being turned on. The indicator light 140 can likewise turn on when the UV source is turned on. The motion detector 150 is configured to detect hands under the bottom 120 of the housing 105 and to transmit a signal to turn the UV source on. The UV source can be configured to turn on for a predetermined period of time in response to receiving the signal from the motion detector. In some embodiments a microcontroller or microprocessor can be coupled to the UV source, the motion detector, the indicator light, and the timer to control the various functions thereof and to allow for modification and/or changes to the operation of the device 100.

The housing 105 can have a length of approximately 4-24 inches, a width of approximately 4-24 inches, and a height of approximately 4-24 inches. The dimensions of the housing 105 are variable within ordinary skill depending upon the particular dwelling or location of the device 100. A smaller housing may be provided for household applications (for example, 4-inch×4-inch×4-inch) and a larger housing may be provided for restaurants and commercial applications (for example, 24-inch×24-inch×24-inch). Although shown as a generally rectangular housing 105 having a flat front, top, back, and sides, any appropriate shape of housing could be implemented. The housing could be rectangular, circular, square, or other appropriate shapes, as will be appreciated.

Figure 2:
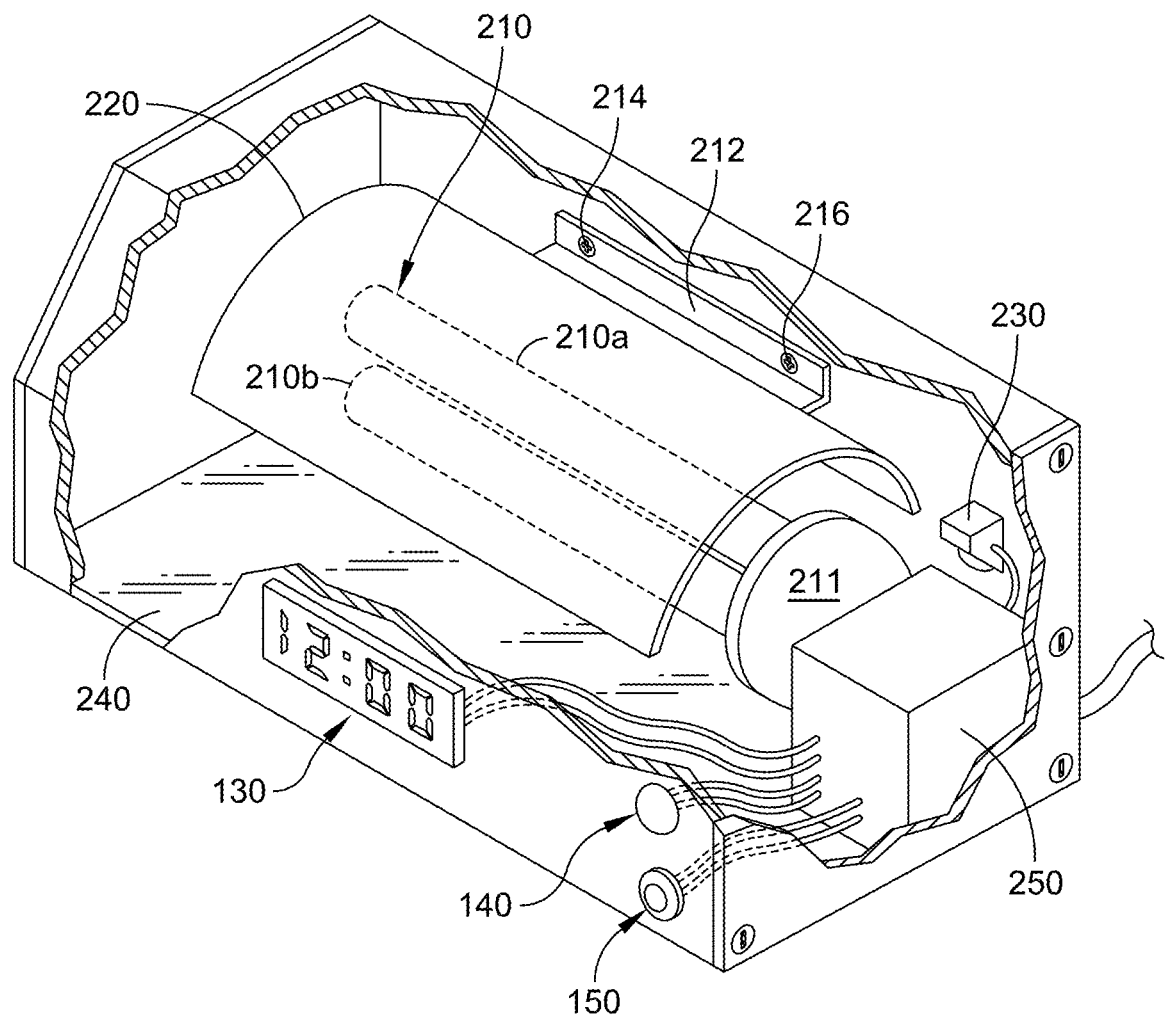
FIG. 2 is a partial cutout view of the device or apparatus of FIG. 1 showing a partial cutout of the housing and revealing the internal components of the housing.

Reference is now made to FIG. 2 showing a partial cutout view of the device with part of the front and top of the housing cutout to reveal the internal components of the housing 105. The device 100 includes a UV source 210. The UV source 210 can be specific to a non-visible light spectrum in a range of 200 nm to 222 nm. The UV source 210 can include a first lamp 210a and a second lamp 210b (or multiple Light-Emitting Diode's "LED's") that are coupled via a lamp receptacle 211 to an AC power supply 250. In some embodiments, the AC power supply 250 could be replaced or supplemented with a DC power supply such as a battery.

A reflector 220 is positioned above the lamp 210 so as to direct rays from the UV source downward through a bottom of the housing. The reflector 220 can be ellipsoidal in shape. The reflector 220 can be secured to the housing 105 by a bracket 212 and appropriate screws or fasteners 214, 216. The UV source is normally off. The reflector is for the purpose of concentrating the light downwardly. One rubs the hands under the lamp assembly 100. The movement of the hands is detected by the motion detector 150 to thus turn on the lamp 210. Since ultraviolet energy in this range is non-visible, the frequency detector 230 determines that the lamp 210 is turned on. The frequency detector 230 can thus activate the "light on" indicator 140. The source 210 is controlled to stay on for a predetermined time (such as approximately 20 seconds) as indicated by a timer 130 responsive to the frequency detector 230.

A frequency detector 230 is also disposed within the housing 105, and coupled to the AC power supply 250. The frequency detector 230 is configured to detect a frequency of rays emitted from the UV source to ensure that the device 100 is operating at the correct frequency to provide the appropriate disinfection needed and/or is used to determine that the UV source is on. In this embodiment, rather than having an open bottom, the housing includes a glass bottom 240 on the housing. The glass bottom can provide a protective surface, to separate hands from the UV lamp when placed underneath, and to prevent someone from inadvertently touching the source. The glass bottom 240 is thus positioned between the UV source and hands when placed under the housing.

The device 100 can be configured such that at least two criteria must be true in order for the device to operate for the amount of time set forth in the timer. For example, in one configuration, the frequency detector must detect the correct frequency and the motion detector must detect the hands or another object under the housing in order for the device to operate for the entire duration. If both of these conditions are true, which can be accomplished with a simple 'AND' logic gate or by other software stored within the microcontroller or microprocessor, then the device continues to operate for the entire duration, with the timer displaying an amount of time remaining. If both condition are not true, the system can output an error signal or error display indicating that the device should not be used.

Figure 3:
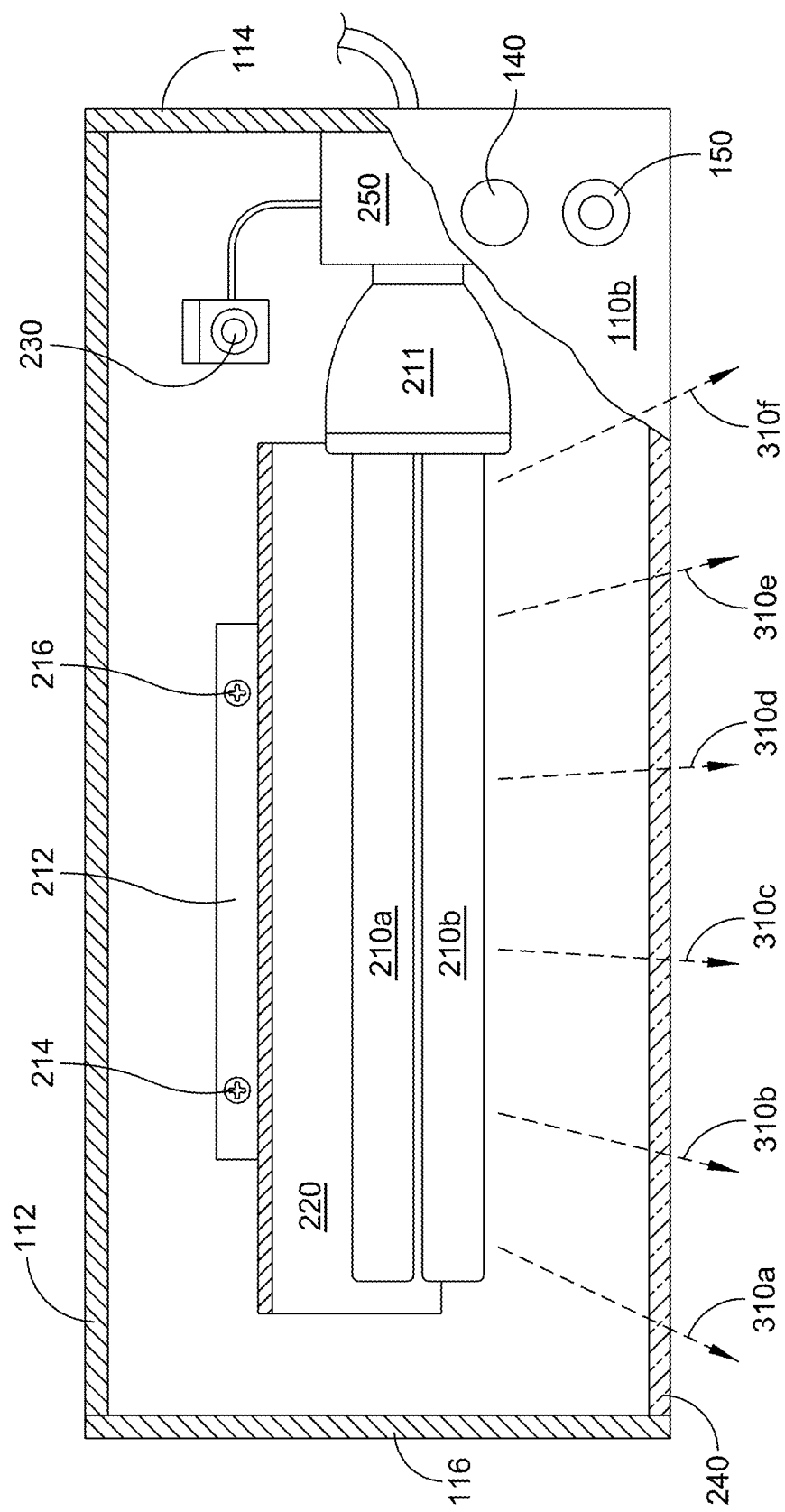
FIG. 3 is a front view of the housing with a partial cutout of the front portion of the housing.

FIG. 3 is a front view of the housing with a partial cutout of the front portion of the housing. As shown, rays 310a, 310b, 310c, 310d, 310e, 310f are directed downward out of the housing. This can be further assisted by the reflector 220 positioned above the source to direct any rays emanating upward and reflect them downward out of the housing and toward hands when placed under the housing. The rays penetrate through the glass bottom 240 as shown, and in some embodiments without a glass bottom the rays would likewise radiate downward out of the open bottom of the housing. In other words, the glass bottom 240 is transparent to the UV rays and they emanate out from the bottom of the housing whether the glass bottom 240 is part of the device or without the glass bottom.

Figure 4:
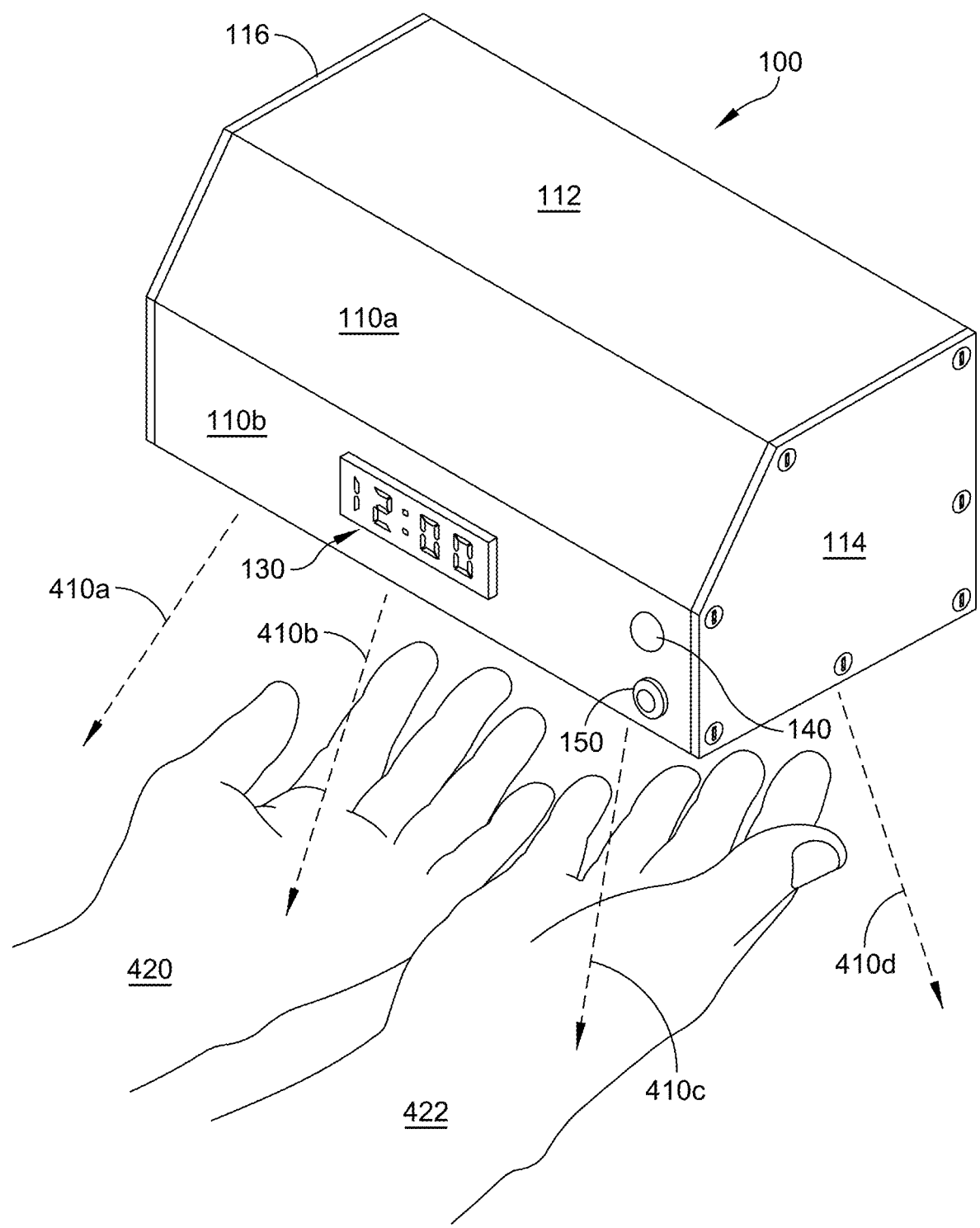
FIG. 4 shows the device in FIG. 2 with the rays emitted downward, out from a bottom of the housing, with the hands disposed under the bottom, according to the present disclosure.

FIG. 4 shows the device in FIG. 2 with the UV rays emitted downward in the direction of arrows 410a, 410b, 410c, 410d, out from a bottom of the device 100, with hands 420, 422 disposed under the bottom of the housing.

Figure 5:
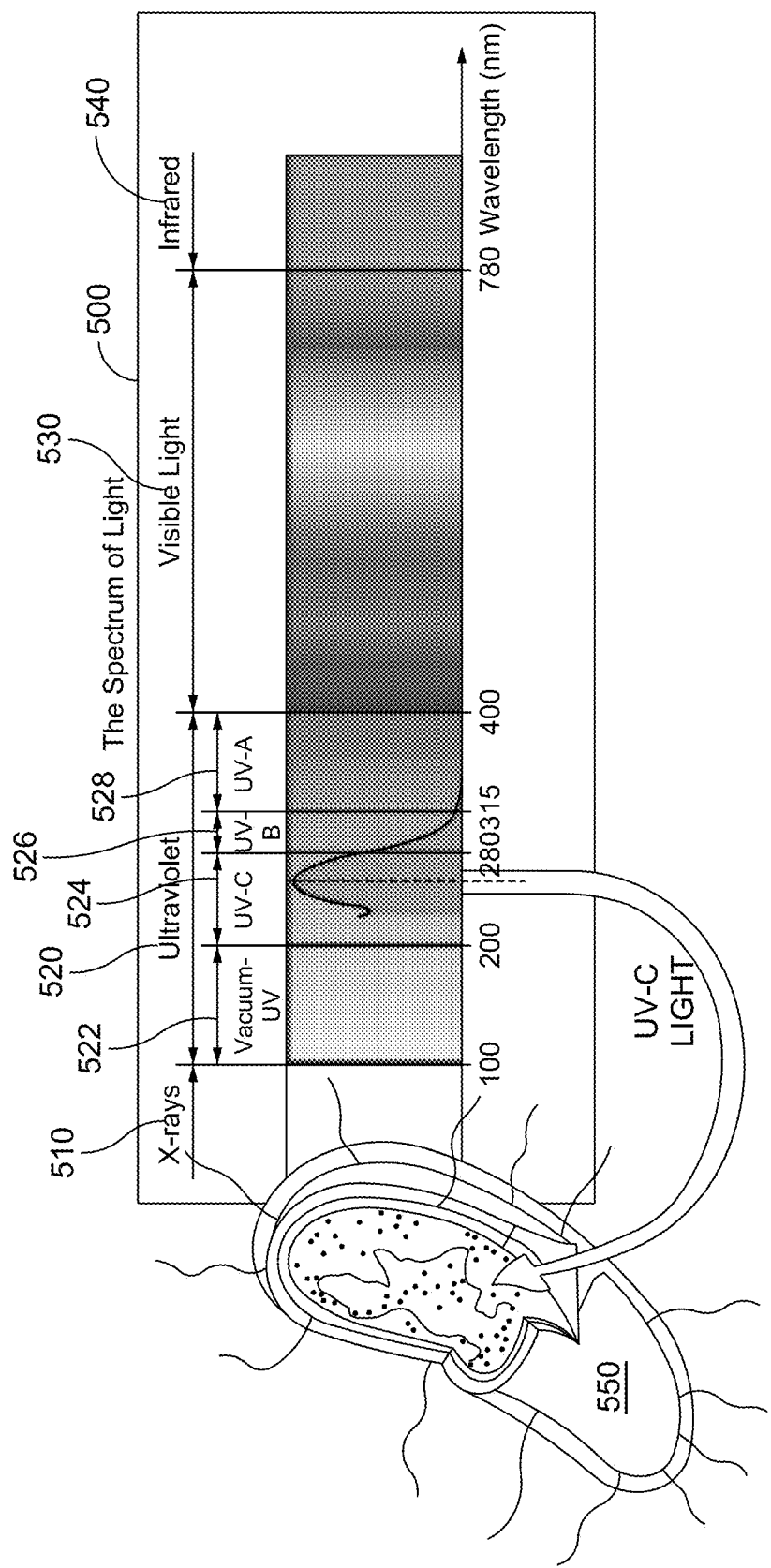
FIG. 5 is an illustration of the preferred spectrum of light that is used according to the present disclosure.

FIG. 5 is an illustration of the preferred spectrum of light that is used according to the present disclosure. Several different bands are shown in the graph 500, including the X-ray band 510, the Ultraviolet band 520, the visible light band 530, and the infrared band 540. Within the Ultraviolet (UV) band, there is the Vacuum-UV band 522, UV-C band 524, UV-C band 526, and UV-A band 528. If has been found that bacteria and viruses 550 are most effectively killed in the UV-C band of 200-222 nm. Thus, this is the desired operating range of the UV source 210 in accordance with the present disclosure.

Figure 6:
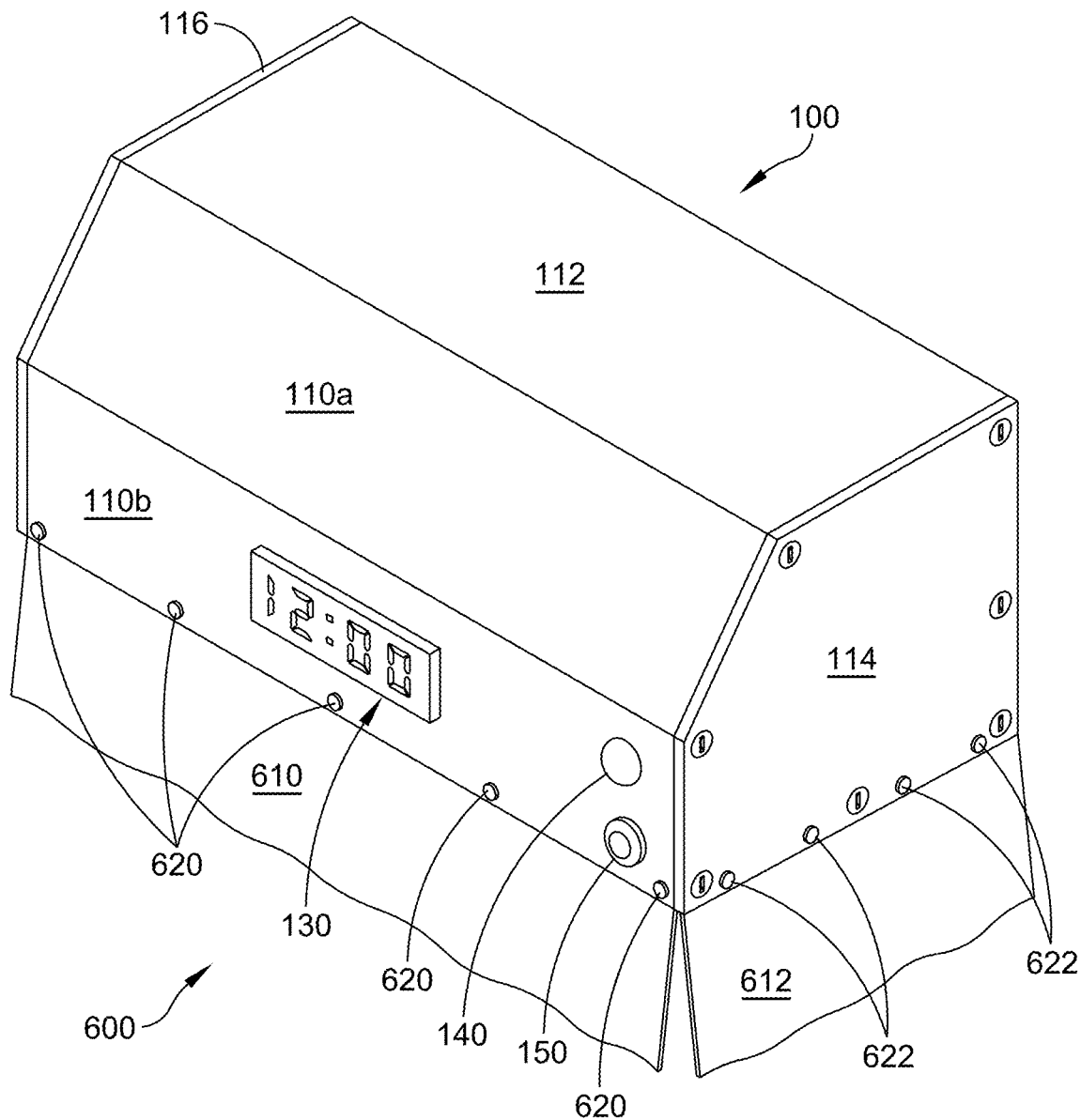
FIG. 6 shows the device as in FIG. 1 with the addition of a curtain, according to the present disclosure.

FIG. 6 shows the device as in FIG. 1 with the addition of an optional curtain, according to the present disclosure. The curtain 600 includes a front flap 610, a side flap 612, a second side flap (not visible) and a rear flap (also not visible). The front flap 610 is secured to the housing by fasteners 620. The side flap 612 is secured to the housing by fasteners 622. The fasteners 620, 622 can be rivets, screws, nails, snaps, or any other appropriate fastener to secure the curtain 600 to the housing 105 of the device 100. The curtain can provide a protective barrier and is disposed about a perimeter of the bottom of the housing. The curtain can be for safety purposes and to reduce potential "light scatter". The curtain can be removable for cleaning as needed. The housing can be solid such that all rays are directed downwardly.

Figure 7:
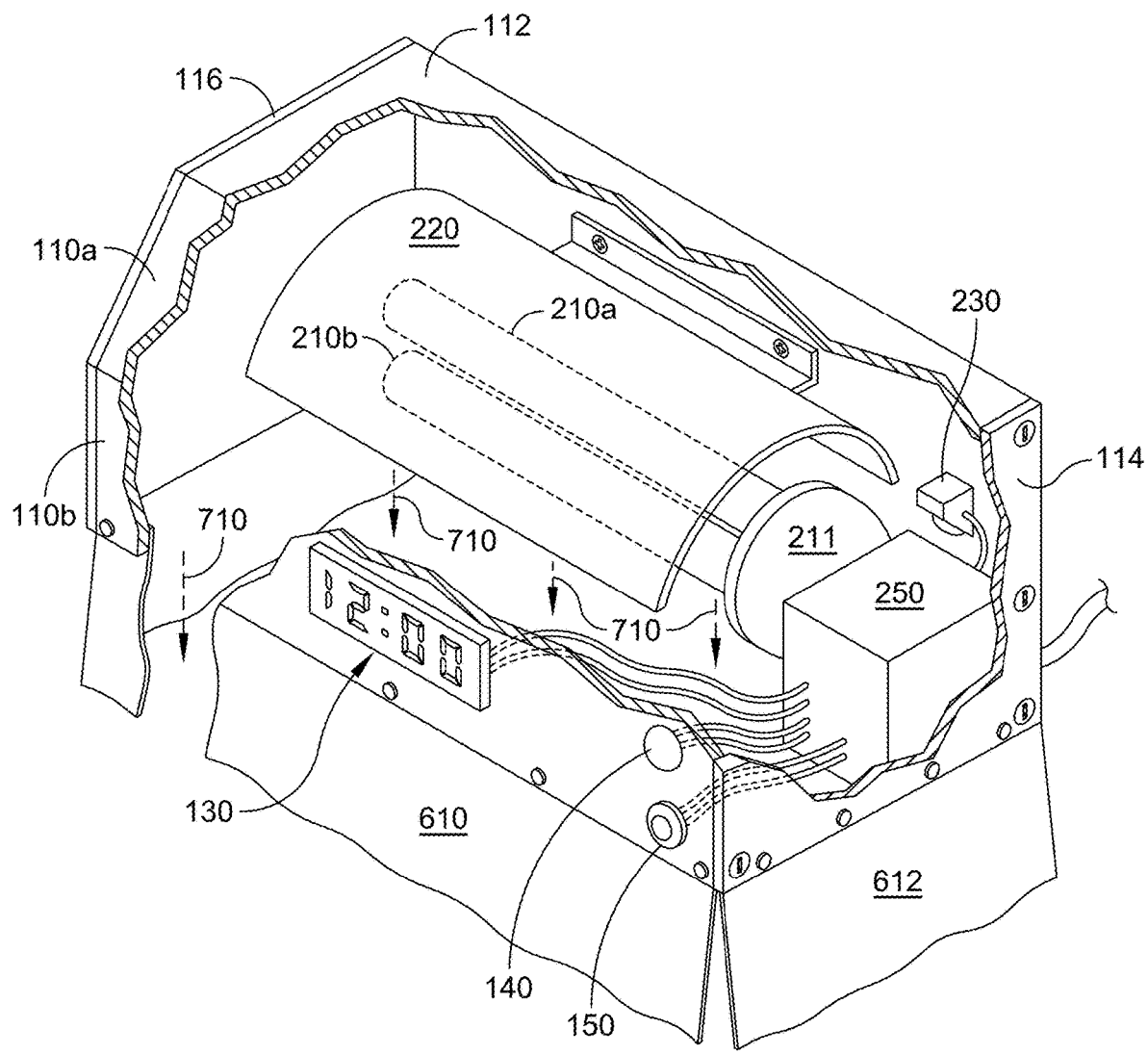
FIG. 7 shows a partial cutout of the device as in FIG. 6 showing the internal components in greater detail and the associated curtain, according to the present disclosure.

FIG. 7 shows a partial cutout of the device as in FIG. 6 showing the internal components in greater detail and the associated curtain, according to the present disclosure. The rays of UV light emanate downward in the direction of arrows 710 out of the bottom of the housing. A user can place their hands within the protective curtain 600 and the rays (arrows 710) will emanate downward to the hands.

Having now described a limited number of embodiments of the present invention, it should now be apparent to those skilled in the art that numerous other embodiments and modifications thereof are contemplated as falling within the scope of the present invention, as defined by the appended claims.

The invention claimed is:

1. A disinfectant device comprising:
a housing that includes a top wall, a front wall, a back wall, a first side wall, and a second side wall, that together form the housing;
said housing having a lower bottom peripheral edge that defines an open bottom of the housing;
a UV lamp disposed within the housing such that UV rays are directed downward through the open bottom of the housing;
said UV lamp being completely contained within the housing and spaced above the lower bottom peripheral edge of the housing;
a reflector that is disposed over the UV lamp for directing rays from the UV lamp downward through the open bottom of the housing;
said reflector being ellipsoidal in shape for concentrating the UV rays downward through the open bottom of the housing;
said reflector spaced below the top wall of the housing and disposed between the top wall of the housing and the UV lamp;
a motion detector configured to detect hands under the open bottom of the housing and to transmit a signal to turn the UV lamp on for a predetermined period of time when hands are detected under the bottom of the housing;
wherein the UV lamp is elongated having a predetermined diameter, and a lower edge of the UV lamp is spaced from the open peripheral bottom edge a distance that is greater than the diameter of the UV lamp;
wherein the ellipsoidal shaped reflector includes a support bracket having a flat wall that is secured to the back wall of the housing by means of one or more fasteners that extend through the bracket flat wall and into the back wall of the housing;
wherein the device further includes an AC power supply that is disposed at the first side wall;
further comprising a frequency detector configured to detect a frequency of the UV rays in order to determine if the UV lamp is turned on;
wherein said UV lamp emits rays of light in a non-visible light spectrum in a range of 200 nm to 222 nm;
a timer mounted at the front wall of the housing and wherein the UV lamp is controlled to stay on for a predetermined time as indicated by the timer responsive to the frequency detector;
an indicator light mounted at the front wall of the housing;
wherein the frequency detector is disposed within the housing adjacent to but spaced from the UV lamp;
wherein the ellipsoidal shaped reflector has a remote distal end that covers a distal end of the UV lamp;
and wherein the distal end of both the ellipsoidal shaped reflector and UV lamp are spaced from the second side wall of the housing.

2. The disinfectant device of claim 1 wherein the frequency detector is attached at the back wall of the housing.

3. The disinfectant device of claim 2 wherein a distal end of the reflector extends beyond the distal end of the UV lamp.

4. A disinfectant device comprising:
a housing that includes a top wall, a front wall, a back wall, a first side wall, and a second side wall, that together form the housing;
said housing having a lower bottom peripheral edge that defines an open bottom of the housing;
a UV lamp disposed within the housing such that UV rays are directed downward through the open bottom of the housing;
said UV lamp being completely contained within the housing and spaced above the lower bottom peripheral edge of the housing;

a reflector that is disposed over the UV lamp for directing rays from the UV lamp downward through the open bottom of the housing;

said reflector being ellipsoidal in shape for concentrating the UV rays downward through the open bottom of the housing;

said reflector spaced below the top wall of the housing and disposed between the top wall of the housing and the UV lamp;

a motion detector configured to detect hands under the open bottom of the housing and to transmit a signal to turn the UV lamp on for a predetermined period of time when hands are detected under the open bottom of the housing;

and on the front wall of the housing disposing one of a timer and indicator light to indicate a duration of the UV lamp being turned on;

and further comprising a protective curtain disposed about the open bottom of the housing.

5. The disinfectant device of claim 4 wherein the protective curtain extends about the entire lower bottom peripheral edge that defines the open bottom of the housing.

6. The disinfectant device of claim 5 wherein the protective curtain is comprised of separate respective front, rear and side flaps.

7. The disinfectant device of claim 6 including fasteners for securing the front, rear and side flaps at the bottom peripheral edge that defines the open bottom of the housing.

* * * * *